United States Patent
Kamiyama et al.

(10) Patent No.: US 10,456,009 B2
(45) Date of Patent: Oct. 29, 2019

(54) IMAGE PROCESSING APPARATUS, IMAGE PROCESSING METHOD, AND COMPUTER-READABLE RECORDING MEDIUM

(71) Applicant: OLYMPUS CORPORATION, Tokyo (JP)

(72) Inventors: Toshiya Kamiyama, Hachioji (JP); Makoto Kitamura, Hachioji (JP); Mitsutaka Kimura, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/817,492

(22) Filed: Nov. 20, 2017

(65) Prior Publication Data

US 2018/0070798 A1    Mar. 15, 2018

Related U.S. Application Data

(63) Continuation of application No. PCT/JP2015/064662, filed on May 21, 2015.

(51) Int. Cl.
*G06K 9/00* (2006.01)
*A61B 1/00* (2006.01)
(Continued)

(52) U.S. Cl.
CPC ...... *A61B 1/00009* (2013.01); *A61B 1/00006* (2013.01); *A61B 1/04* (2013.01);
(Continued)

(58) Field of Classification Search
None
See application file for complete search history.

(56) References Cited

U.S. PATENT DOCUMENTS

| 8,160,329 B2 | 4/2012 | Inoue | |
|---|---|---|---|
| 2011/0280443 A1* | 11/2011 | Kitamura | G06T 7/0012 |
| | | | 382/103 |
| 2015/0092993 A1 | 4/2015 | Kanda et al. | |

FOREIGN PATENT DOCUMENTS

| CN | 104363815 A | 2/2015 |
|---|---|---|
| JP | 2002165757 A | 6/2002 |

(Continued)

OTHER PUBLICATIONS

International Search Report dated Aug. 11, 2015 issued in PCT/JP2015/064662.

(Continued)

*Primary Examiner* — Stephen P Coleman

(74) *Attorney, Agent, or Firm* — Scully, Scott, Murphy & Presser, P.C.

(57) ABSTRACT

An image processing apparatus includes: a candidate region detection unit configured to detect, from an image acquired by imaging inside a lumen of a living body, a candidate region for a specific region that is a region where a specific part in the lumen has been captured; a candidate region information acquiring unit configured to acquire information related to the candidate region detected by the candidate region detection unit; an identification means determination unit configured to determine an identification means for identification of, based on the information related to the candidate region, whether or not the candidate region is the specific region; and an identification unit configured to identify whether or not the candidate region is the specific region by using the identification means determined by the identification means determination unit.

11 Claims, 17 Drawing Sheets

(51) Int. Cl.
*A61B 1/04* (2006.01)
*G06T 7/00* (2017.01)
*G06T 7/73* (2017.01)
*G06T 7/44* (2017.01)
*G06T 7/90* (2017.01)
*G06T 7/62* (2017.01)

(52) U.S. Cl.
CPC .............. *G06T 7/0012* (2013.01); *G06T 7/44* (2017.01); *G06T 7/62* (2017.01); *G06T 7/75* (2017.01); *G06T 7/90* (2017.01); *G06T 2207/10024* (2013.01); *G06T 2207/30092* (2013.01); *G06T 2207/30096* (2013.01)

(56) References Cited

FOREIGN PATENT DOCUMENTS

| | | |
|---|---|---|
| JP | 2008036243 A | 2/2008 |
| JP | 2008234623 A | 10/2008 |

\* cited by examiner

FIG.15
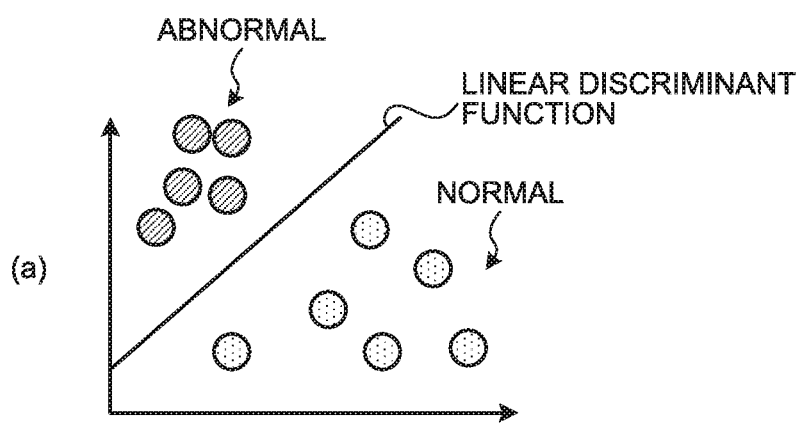
(a)
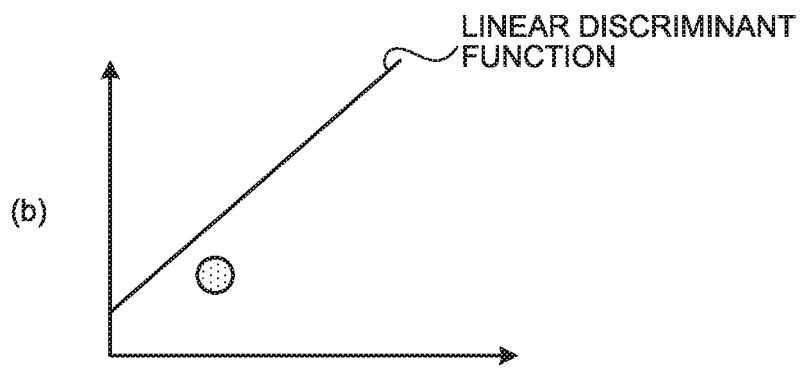
(b)

IMAGE PROCESSING APPARATUS, IMAGE PROCESSING METHOD, AND COMPUTER-READABLE RECORDING MEDIUM

CROSS-REFERENCE TO RELATED APPLICATION

This application is a continuation of International Application No. PCT/JP2015/064662, filed on May 21, 2015, the entire contents of which are incorporated herein by reference.

BACKGROUND

1. Technical Field

The disclosure relates to an image processing apparatus, an image processing method, and a computer-readable recording medium, for image processing of an image acquired by imaging inside a lumen of a living body.

2. Related Art

A technique has been known, which is for detecting or identifying an abnormal region, such as a tumor or a lesion, for an intraluminal image that is an image acquired by imaging inside a lumen (inside a gastrointestinal tract) of a living body by use of a medical observation apparatus, such as an endoscope, a capsule endoscope, or the like.

For example, in Japanese Patent Application Laid-open No. 2008-234623 (hereinafter, Patent Literature 1), a category identification apparatus is disclosed, which includes: an overall identifier that identifies a category that an image belongs to, based on overall feature data representing features of the overall image; and a partial identifier that identifies a category that the image belongs to, based on partial feature data representing partial features in the image.

In the above mentioned Patent Literature 1, the overall identifier identifies a scene of an input image by use of a support vector machine that uses, as feature data, chromatic dispersion, a color average, and the like of the overall input image. The partial identifier identifies a scene of the input image by use of a support vector machine that treats, as feature data, chromatic dispersion, a color average, and the like of a certain region in the input image. For an image, for which the overall identifier and the partial identifier have been unable to identify a scene thereof, an integrated identifier finds a final identification result, based on respective results of the identification by the overall identifier and the partial identifier.

SUMMARY

In some embodiments, an image processing apparatus includes: a candidate region detection unit configured to detect, from an image acquired by imaging inside a lumen of a living body, a candidate region for a specific region that is a region where a specific part in the lumen has been captured; a candidate region information acquiring unit configured to acquire information related to the candidate region detected by the candidate region detection unit; an identification means determination unit configured to determine an identification means for identification of, based on the information related to the candidate region, whether or not the candidate region is the specific region; and an identification unit configured to identify whether or not the candidate region is the specific region by using the identification means determined by the identification means determination unit.

In some embodiments, an image processing method includes: detecting, from an image acquired by imaging inside a lumen of a living body, a candidate region for a specific region that is a region where a specific part in the lumen has been captured; acquiring information related to the detected candidate region; determining an identification means for identification of, based on the information related to the candidate region, whether or not the candidate region is the specific region; and identifying whether or not the candidate region is the specific region by using the determined identification means.

In some embodiments, a non-transitory computer-readable recording medium recording an image processing program is provided. The program causes a computer to execute: detecting, from an image acquired by imaging inside a lumen of a living body, a candidate region for a specific region that is a region where a specific part in the lumen has been captured; acquiring information related to the detected candidate region; determining an identification means for identification of, based on the information related to the candidate region, whether or not the candidate region is the specific region; and identifying whether or not the candidate region is the specific region by using the determined identification means.

The above and other features, advantages and technical and industrial significance of this disclosure will be better understood by reading the following detailed description of presently preferred embodiments of the disclosure, when considered in connection with the accompanying drawings.

BRIEF DESCRIPTION OF THE DRAWINGS

FIG. 15 is a schematic diagram for explanation of classification by a linear discriminant function;

DETAILED DESCRIPTION

Hereinafter, image processing apparatuses, image processing methods, and image processing programs, according to embodiments of the disclosure will be described, while reference is made to the drawings. The disclosure is not limited by these embodiments. Further, the same signs are used to refer to the same portions throughout the drawings.

First Embodiment

Figure 1:
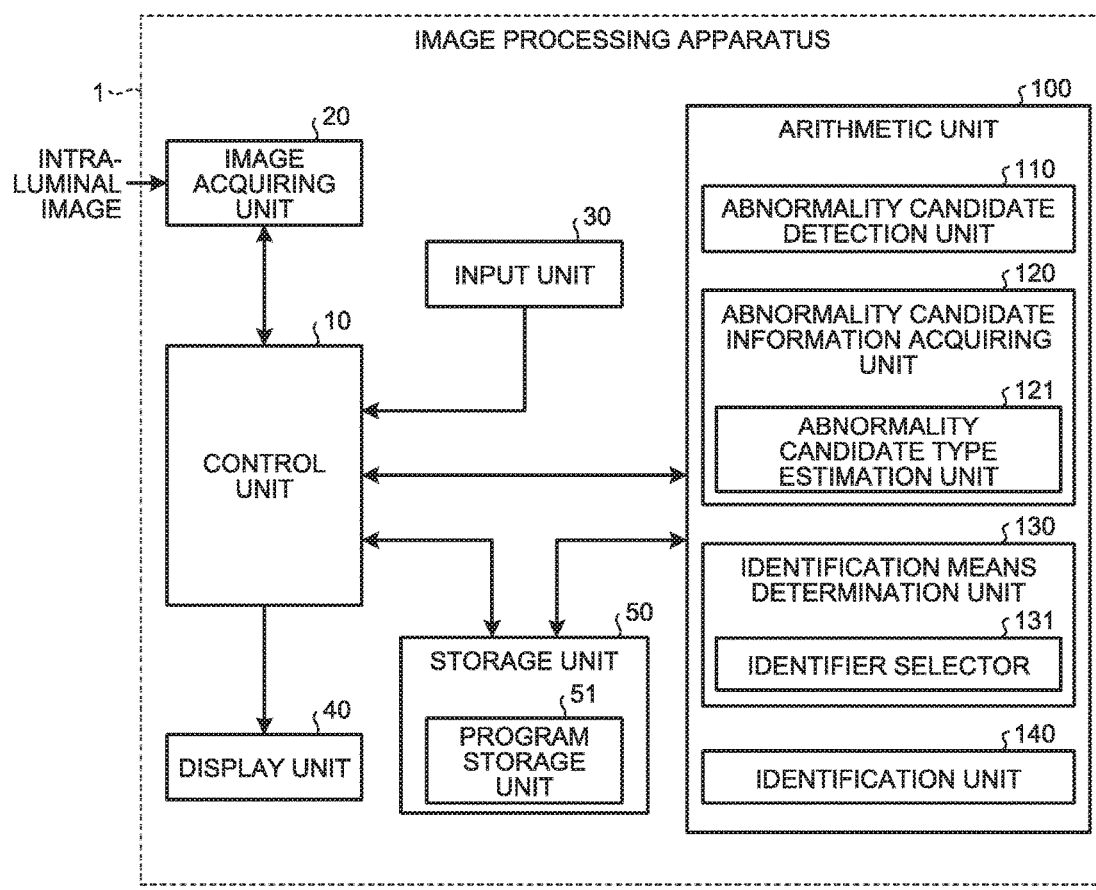
FIG. 1 is a block diagram illustrating a configuration of an image processing apparatus according to a first embodiment of the disclosure.

FIG. 1 is a block diagram illustrating a configuration of an image processing apparatus according to a first embodiment of the disclosure. An image processing apparatus 1 according to the first embodiment is an apparatus that detects a specific region from an intraluminal image by executing image processing on an image acquired by a medical observation apparatus, such as an endoscope, imaging inside a lumen of a living body, that is, the intraluminal image, the specific region being a region where a specific part inside the lumen has been captured. In this first embodiment, as the specific region, a region where a part considered to be a lesion or an abnormality, such as bleeding, reddening, clotted blood, a tumor, erosion, an ulcer, aphtha, a villus abnormality, or the like, has been captured, that is, an abnormal region, is detected. These abnormalities are able to be broadly classified into three types, which are: vascular abnormality, such as bleeding, reddening, and clotted blood; neoplastic abnormality, such as polyps; and mucosal abnormality, such as erosion, ulcers, aphtha, and villus abnormalities. Further, the intraluminal image is normally a color image having pixel levels (pixel values) for red (R), green (G), and blue (B) wavelength components at each pixel position thereof.

As illustrated in FIG. 1, the image processing apparatus 1 includes: a control unit 10 that controls operation of the overall image processing apparatus 1; an image acquiring unit 20 that acquires image data generated by the medical observation apparatus imaging inside a lumen; an input unit 30 that inputs a signal according to an operation from outside, into the control unit 10; a display unit 40 that displays various types of information and images; a storage unit 50 that stores therein the image data acquired by the image acquiring unit 20 and various programs; and an arithmetic unit 100 that executes predetermined image processing on the image data.

The control unit 10 is configured by use of: a general purpose processor, such as a central processing unit (CPU), or a special purpose processor, such as any arithmetic circuit that executes a specific function, like an application specific integrated circuit (ASIC). If the control unit 10 is a general purpose processor, by reading the various programs stored in the storage unit 50, the control unit 10 executes transfer or the like of instructions and data to the respective units forming the image processing apparatus 1, and comprehensively controls the operation of the overall image processing apparatus 1. Further, if the control unit 10 is a special purpose processor, the processor may execute various types of processing alone, or the processor and the storage unit 50 may execute various types of processing in cooperation or combination with each other by using various data and the like stored in the storage unit 50.

The image acquiring unit 20 is configured, as appropriate, according to a form of a system including the medical observation apparatus. For example, if the medical observation apparatus is connected to the image processing apparatus 1, the image acquiring unit 20 is formed of an interface that takes in image data generated by the medical observation apparatus. Further, if a server to store therein image data generated by the medical observation apparatus is to be installed, the image acquiring unit 20 is formed of a communication device or the like connected to the server, and acquires the image data by executing data communication with the server. Or, image data generated by the medical observation apparatus may be transferred by use of a portable storage medium, and in this case, the image acquiring unit 20 is formed of a reader device, to which this portable storage medium is detachably attached, and which reads out the image data of an image stored therein.

The input unit 30 is realized by an input device, such as, for example, a keyboard and a mouse, a touch panel, and/or various switches, and outputs an input signal generated according to an operation on this input device from outside, to the control unit 10.

The display unit 40 is realized by a display device, such as an LCD or an EL display, and under control by the control unit 10, displays thereon various screens including the intraluminal image.

The storage unit 50 is realized by any of: various IC memories, such as a ROM and a RAM, like rewritable flash memories; a hard disk that is built therein or connected via a data communication terminal; an information storage device, such as a CD-ROM, and an information writing and reading device for the information storage device; and the like. The storage unit 50 stores therein image data of the intraluminal image acquired by the image acquiring unit 20, as well as a program for the image processing apparatus 1 to be caused to operate and for the image processing apparatus 1 to be caused to execute various functions, data used during the execution of this program, and the like. Specifically, the storage unit 50 has a program storage unit 51 that stores therein an image processing program for detection of an abnormal region from an intraluminal image. Further, the storage unit 50 stores therein information, such as identification criterions used in the image processing.

The arithmetic unit 100 is configured by use of a general purpose processor, such as a CPU, or a special purpose processor, such as an arithmetic circuit that executes a specific function, such as an ASIC. If the arithmetic unit 100 is a general purpose processor, by reading the image processing program stored in the program storage unit 51, the arithmetic unit 100 executes image processing for detection of an abnormal region from the acquired intraluminal image. Further, if the arithmetic unit 100 is a special purpose processor, the processor may execute various types of processing alone, or the processor and the storage unit 50 may execute the image processing in cooperation or combination with each other by using various data or the like stored in the storage unit 50.

Next, a configuration of the arithmetic unit 100 will be described. As illustrated in FIG. 1, the arithmetic unit 100 includes: an abnormality candidate detection unit 110 serving as a candidate region detection unit that detects a candidate region for an abnormal region (hereinafter, referred to as "abnormality candidate region") from an intraluminal image; an abnormality candidate information acquiring unit 120 serving as a candidate region information acquiring unit that acquires information related to the abnormality candidate region detected by the abnormality candidate detection unit 110; an identification means determination unit 130 that determines, based on the information related to the abnormality candidate region, an identification means for identification of whether or not the abnormality candidate region is an abnormal region; and an identification unit 140 that identifies whether or not the abnormality candidate region is an abnormal region by using the identification means determined by the identification means determination unit 130.

The abnormality candidate detection unit 110: divides the intraluminal image into more than one region; calculates color feature data, shape feature data, and texture feature data for each divided region; finds degrees of coincidence between abnormality models that have been learnt beforehand and these feature data; and thereby determines whether or not each region is an abnormality candidate region.

The abnormality candidate information acquiring unit 120 acquires information related to an abnormality candidate region. In this first embodiment, the abnormality candidate information acquiring unit 120: includes an abnormality candidate type estimation unit 121; and acquires, as the information related to the abnormality candidate region, a type of abnormality that the abnormality candidate region is estimated to belong to, that is, any of: vascular abnormality, such as bleeding, reddening, and clotted blood; neoplastic abnormality, such as polyps; and mucosal abnormality, such as erosion, ulcers, aphtha, and villus abnormalities.

The identification means determination unit 130 determines, based on the information related to the abnormality candidate region, an identification means to be used in identification of the abnormality candidate region. In this first embodiment, the identification means determination unit 130 includes an identifier selector 131.

As identification means for abnormal regions, more than one identifier having different identification accuracies according to the above described types of abnormality are available. For example, vascular abnormality, such as bleeding, reddening, and clotted blood, has a large difference in color from that of a normal mucosal surface. Therefore, for identification of vascular abnormality, when a color feature data identifier that executes identification based on color feature data, such as color ratio, hue, and chroma, is used, accurate identification is able to be executed. Further, neoplastic abnormality, such as polyps, has a large difference in shape from that of a structure of a normal mucosal surface, the difference being, for example, that the shape is circularly bulged. Therefore, for identification of neoplastic abnormality, when a shape feature data identifier that executes identification based on shape feature data, such as circularity, area, and Feret's diameter, is used, accurate identification is able to be executed. Mucosal abnormality, such as erosion, ulcers, aphtha, and villus abnormalities, has a change in surface structure generated therein, with a change in color, like redness or whiteness, according to inflammation, from a normal mucosal surface. Therefore, for identification of mucosal abnormality, when, together with a color feature data identifier, a texture feature data identifier, which executes identification based on texture feature data, such as intensity of a high frequency component calculated from Local Binary Pattern (LBP), Difference of Gaussian (DoG), or the like, is used, accurate identification is able to be executed.

The identifier selector 131 acquires information on which one of vascular abnormality, neoplastic abnormality, and mucosal abnormality, the abnormality candidate region belongs to, and selects an identifier according to the type of abnormality that the abnormality candidate region belongs to.

The identification unit 140 identifies whether or not the abnormality candidate region is an abnormal region by using the identification means determined by the identification means determination unit 130, that is, one of: a color feature data identifier; a shape feature data identifier; and a combination of a color feature data identifier and a texture feature data identifier.

Figure 2:
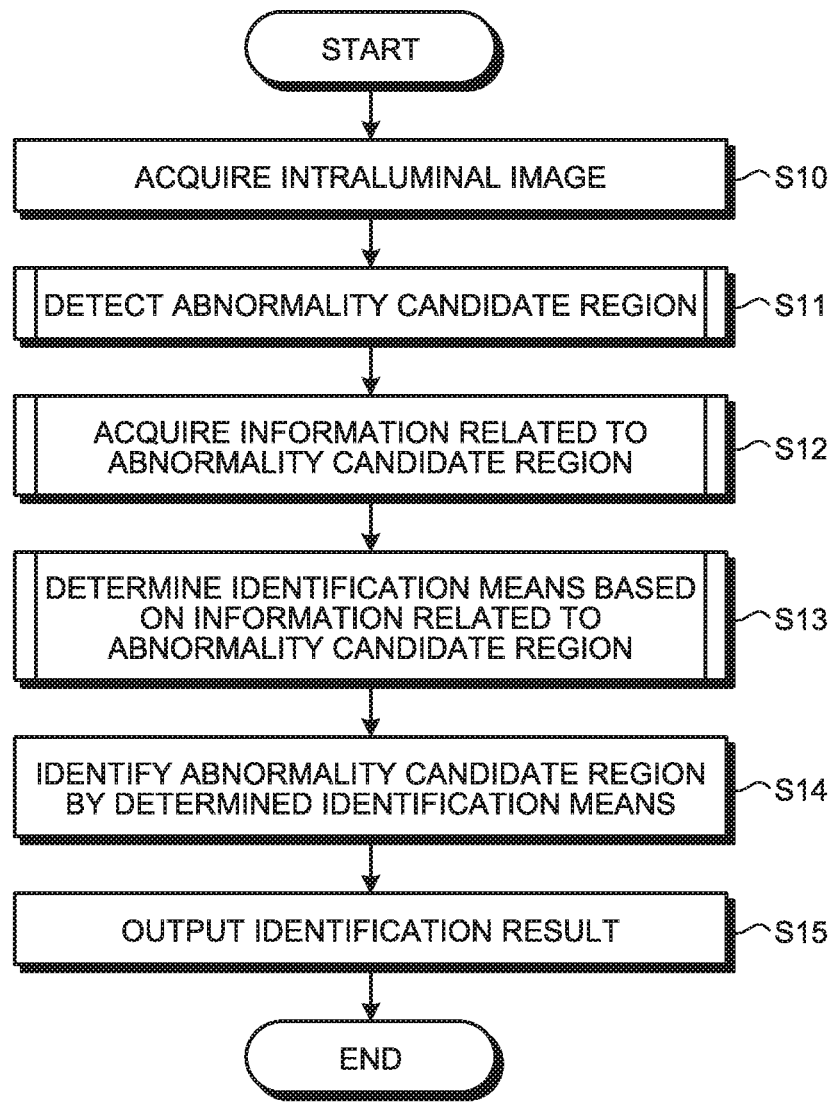
FIG. 2 is a flow chart illustrating operation of the image processing apparatus illustrated in FIG. 1.

Next, the operation of the image processing apparatus 1 will be described. FIG. 2 is a flow chart illustrating processing by the image processing apparatus 1 on an intraluminal image to be processed.

Firstly, at Step S10, the image processing apparatus 1 acquires an intraluminal image via the image acquiring unit 20. In this first embodiment, an intraluminal image, which is generated by the endoscope executing imaging through irradiation of inside of a lumen with illumination light (white light) including R, G, and B wavelength components, and which has pixel values (R value, G value, and B value) corresponding to these wavelength components at each pixel position thereof, is acquired.

Figure 3:
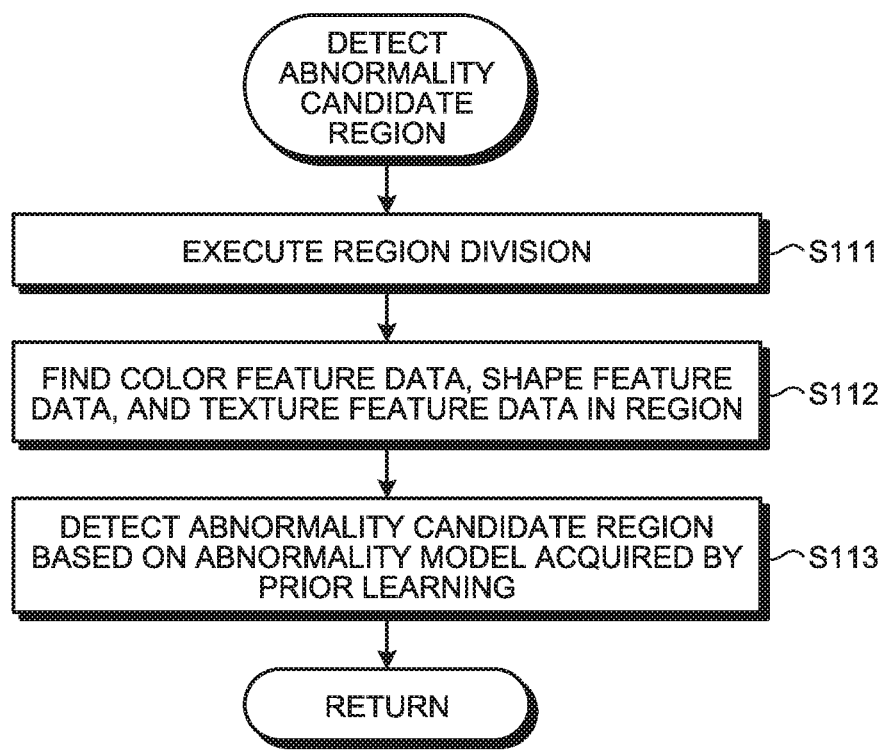
FIG. 3 is a flow chart illustrating a process for detection of an abnormality candidate region illustrated in FIG. 2.

At subsequent Step S11, the abnormality candidate detection unit 110 detects an abnormality candidate region from the intraluminal image. FIG. 3 is a flow chart illustrating a process for the detection of an abnormality candidate region.

At Step S111, the abnormality candidate detection unit 110 executes region division on the intraluminal image (reference: Computer Graphic Arts Society, "Digital Image Processing", 2nd Edition, Page 196). In detail, region division processing by integration of adjacent similar pixels is executed. That is: pixels are searched by raster scanning; assignment of a label to adjacent pixels having the same pixel value as that of a pixel of interest is executed for the entire image, the label being the same as that of the pixel of interest; and thereafter, a process, in which an average value of pixel values of pixels having the same label is found, and a process, in which groups from adjacent groups of pixels are integrated together, the groups having a minimum difference between average values of their pixel values, are repeated. Thereby, the intraluminal image is able to be divided into plural regions, each of which is formed of a group of pixels having close pixel values. Region division may be executed by any of various known means, other than the integration of adjacent similar pixels.

At subsequent Step S112, the abnormality candidate detection unit 110 finds color feature data, shape feature data, and texture feature data in the region, for each of the regions that the intraluminal image is divided into. Based on pixel values (R value, G value, and B value) of each pixel, average values of color ratios, G value/R value and B value/G value, are calculated as the color feature data. Or, instead of the color ratios, the R, G, and B values as they are, or dispersion values, chroma, hue, color differences, or the like of R, G, and G values may be used; or instead of their average values, statistics, such as medians or modes, may be used.

Further, a circularity, a Feret's diameter, and an area of the region are calculated as the shape feature data (reference: Computer Graphic Arts Society, "Digital Image Processing", 2nd Edition, Pages 182 to 183). The circularity is given by $4\pi S/L^2$, where the area of the region is "S" and a perimeter of the region is "L"; and the closer to "1" this value is, the closer the shape is to a perfect circle. The area, "S", is given as a total number of pixels included in the region to be processed. Furthermore, the perimeter, "L", may be found by eight-connection contour tracing for the region to be processed (Computer Graphic Arts Society, "Digital Image Processing", 2nd Edition, Pages 178 to 179). That is, a tracing process, in which, with a labeled pixel being a base point, pixels around the base point are searched and a move to the next labeling pixel is executed, is repeated. Where the number of tracing moves over upper, lower, left, and right pixels is $C_1$, and the number of diagonal tracing moves is $C_2$; the perimeter, "L", is given by $(C_1 + \sqrt{2} \times C_2)$.

Two types of values, a horizontal Feret's diameter and a vertical Feret's diameter, are used as the Feret's diameter. Further, the area is, as described above, the total number of pixels included in the region. In addition, as the shape feature data, histogram-of-oriented-gradients (HOG) feature data, scale-invariant-feature-transform (SIFT) feature data, or the like may be used.

Local Binary Pattern (LBP), which is a known technique, is used, for example, as the texture feature data (reference: Ryusuke Nosaka, et al., "2. LBP Histogram", from "Feature Extraction Based on Adjacency Relationship of Local Binary Patterns", The Technical Report of The Proceeding of The Institute of Electronics, Information and communication Engineers, Pattern Recognition and Media Understanding, PRMU 2011-69, Pages 75 to 80 (Sep. 5 to 6, 2011)). An LBP is feature data representing magnitude relations between pixel values of a pixel of interest and pixels in eight directions around the pixel of interest, with a histogram of 2-to-the-power-of-8 dimensions, that is, 256 dimensions. When LBPs are applied to this first embodiment, magnitude relations between pixel values of each pixel in the region and pixels in eight directions around that pixel are represented by a histogram, and a value added up thereof is used as the texture feature data.

Or, in the region, conversion to a specific frequency component image may be executed, and an average value of intensities of the specific frequency component may be used as the texture feature data. For example, Difference of Gaussian (DoG), which is a known technique, may be used as a method for the conversion to the specific frequency component image (reference: Advanced Communication Media Co., Ltd., "Computer Vision Forefront Guide 2", Pages 7 to 12).

Further, angular second moment, contrast, entropy, or the like of a cooccurrence matrix (reference: University of Tokyo Press, "Image Analysis Handbook", Pages 517 to 521) may be used as the texture feature data.

At subsequent Step S113, the abnormality candidate detection unit 110 detects, based on an abnormality model acquired by prior learning, an abnormality candidate region. In detail, the color feature data, the shape feature data, and the texture feature data found in Step S112 are respectively treated as vectors, the respective vector sequences are combined together, and a feature vector is generated for each region. When the feature vector is generated, normalization is executed, and each vector is weighted as necessary. Determination is then executed by use of a discriminant function for abnormality, the discriminant function having been generated beforehand.

Specifically, a decision index P(x) based on a stochastic model given by Equation (1) below is calculated.

$$P(x) = \frac{1}{(2\pi)^{k/2} \times |Z|^{1/2}} \exp\left\{(x-\mu)^t \times \left(-\frac{1}{2}\right) Z^{-1} \times (x-\mu)\right\} \quad (1)$$

The decision index P(x) is an index indicating whether or not the feature vector of the abnormality candidate region appears to be a feature vector of an abnormal region. The larger the value of the decision index P(x) is, the more it is able to be said that the abnormality candidate region appears to be an abnormal region. That is, the decision index P(x) indicates a degree of coincidence between the abnormality candidate region and an abnormal region. Further, the symbol, "x", expressed in Equation (1) represents a feature vector (k rows and one column) of the abnormality candidate region subjected to the determination. Furthermore, the symbol $\mu$ is an average vector (k rows and one column) of feature vectors in plural abnormal region samples acquired beforehand. The symbol, "Z", is a variance-covariance matrix (k rows and k columns) of the feature vectors in the plural abnormal region samples acquired beforehand. The symbol |Z| is a determinant of this matrix, "Z", and the symbol $Z^{-1}$ is an inverse matrix of the matrix, "Z".

The decision index P(x) indicating abnormal-region-ness of the abnormality candidate region is calculated by use of Equation (1), and if this decision index is equal to or larger than a threshold, that region is detected as an abnormality candidate region. Thereafter, the process is returned to the main routine.

At Step S12 subsequent to Step S11, the abnormality candidate information acquiring unit 120 acquires information related to the abnormality candidate region. Specifically, the abnormality candidate type estimation unit 121 acquires a type of abnormality that the abnormality candidate region is estimated to belong to, that is, one of vascular abnormality, neoplastic abnormality, and mucosal abnormality.

Figure 4:
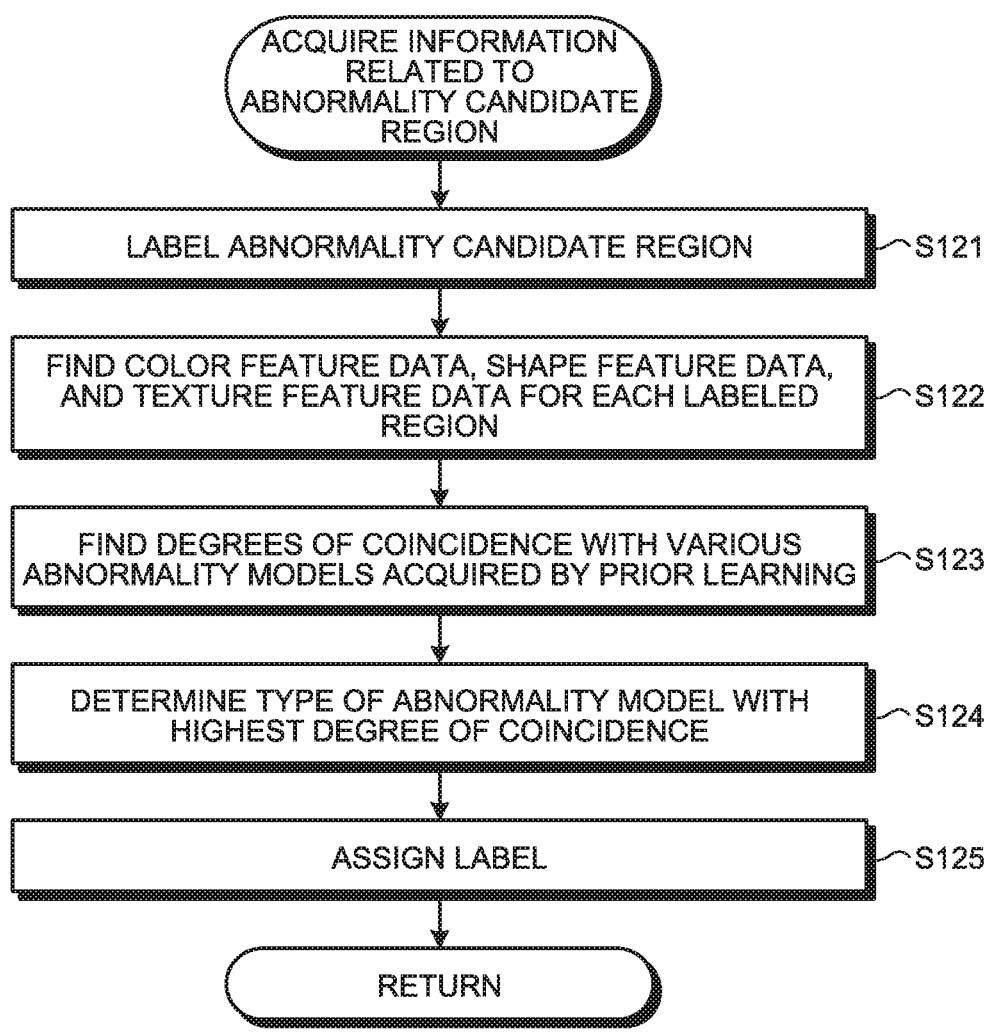
FIG. 4 is a flow chart illustrating an acquisition process for information related to the abnormality candidate region illustrated in FIG. 2.

FIG. 4 is a flow chart illustrating an acquisition process for the information related to the abnormality candidate region. At Step S121, the abnormality candidate type estimation unit 121 labels abnormality candidate regions (reference: Computer Graphic Arts Society, "Digital Image Processing", 2nd Edition, Pages 181 to 182). That is, a process, in which the same label is assigned to abnormality candidate regions having the same connected component, and different labels are assigned to abnormality candidate regions having different connected components, is executed.

At subsequent Step S122, the abnormality candidate type estimation unit 121 finds color feature data, shape feature data, and texture feature data for each labeled region. Specifically, similarly to Step S112, average values of color ratios or the like are calculated as the color feature data, a circularity, a Feret's diameter, an area, and the like of the region are calculated as the shape feature data, and an LBP or the like is calculated as the texture feature data.

At subsequent Step S123, the abnormality candidate type estimation unit 121 finds degrees of coincidence with various abnormality models acquired by prior learning. In detail, for each labeled region, the color feature data, shape feature data, and texture feature data that have been found in Step S122 are integrated together and thereby a feature vector is generated. When the feature vector is generated, normalization is executed, and each vector is weighted as necessary.

A decision index $P(x)_{blood\ vessel}$ for vascular abnormality is calculated by application of the feature vector of each labeled region and feature vectors of plural samples of vascular abnormality, such as bleeding, reddening, and clotted blood, which have been acquired beforehand, to the decision index P(x) expressed by Equation (1). Similarly, a decision index $P(x)_{tumor}$ for neoplastic abnormality is calculated by application of feature vectors of plural samples of neoplastic abnormality, such as polyps, which have been acquired beforehand, to the decision index P(x) of Equation (1). A decision index $P(x)_{mucosa}$ for mucosal abnormality is calculated similarly by application of feature vectors of plural samples of mucosal abnormality, such as erosion, ulcers, aphtha, and villus abnormalities, which have been acquired beforehand, to the decision index P(x) of Equation (1). Values of these decision indices $P(x)_{blood\ vessel}$, $P(x)_{tumor}$, and $P(x)_{mucosa}$ indicate degrees of coincidence of each labeled region with the various abnormality models.

At subsequent Step S124, the abnormality candidate type estimation unit 121 determines a type of the abnormality model with the highest degree of coincidence. That is, the abnormality with the largest one of the values of the decision indices $P(x)_{blood\ vessel}$, $P(x)_{tumor}$ and $P(x)_{mucosa}$ calculated in Step S123 is estimated as the type of the abnormality candidate region.

At subsequent Step S125, the abnormality candidate type estimation unit 121 assigns a label indicating the type of the abnormality candidate region, to each pixel in the abnormality candidate region. Thereafter, the process is returned to the main routine.

At Step S13 subsequent to Step S12, the identification means determination unit 130 determines an identification means, based on the information related to the abnormality candidate region, that is, the type of abnormality estimated for the abnormality candidate region, the information having been acquired in Step S12. In detail, the identifier selector 131 selects an identifier according to the type of abnormality of the abnormality candidate region.

Figure 5:
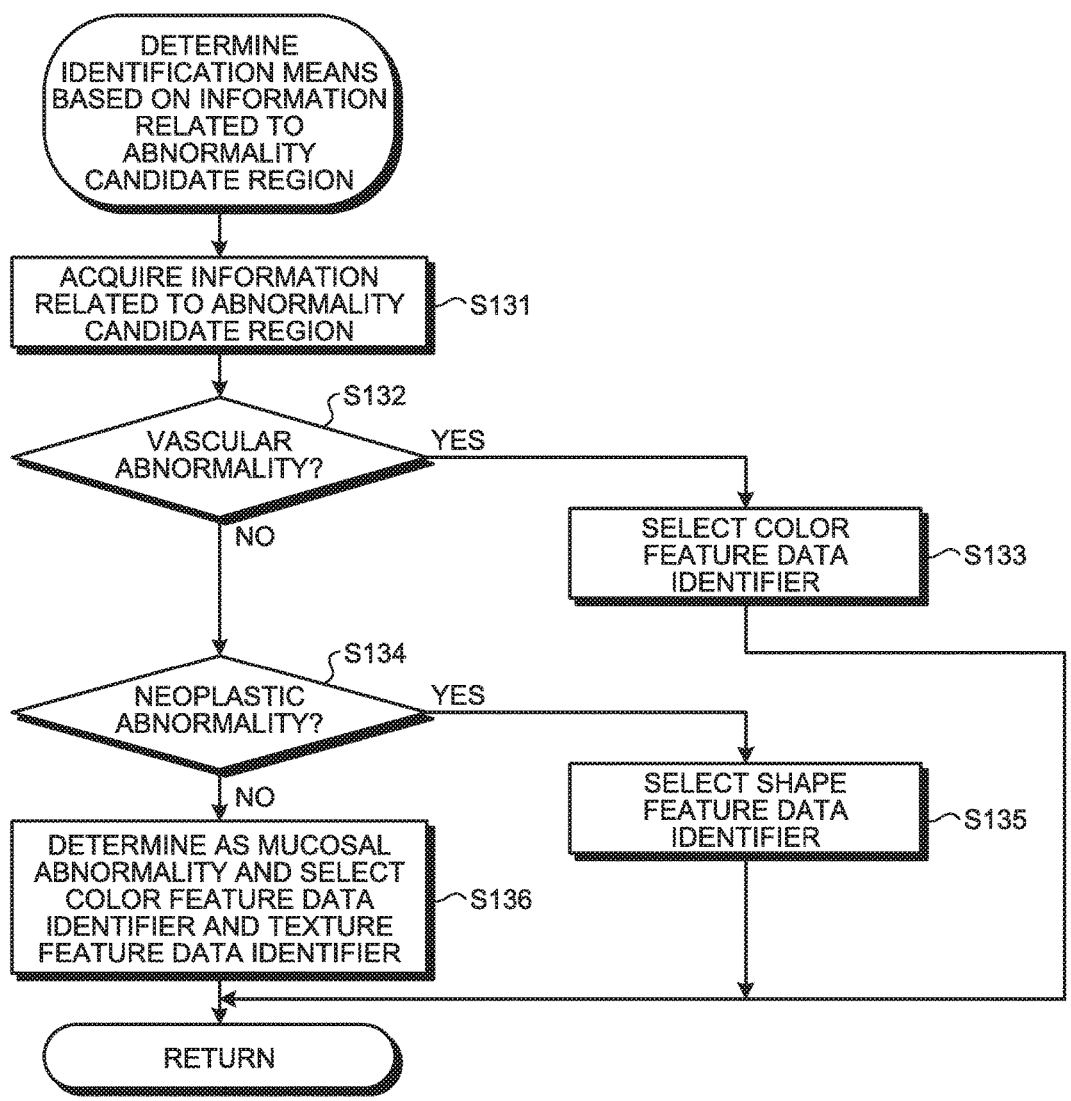
FIG. 5 is a flow chart illustrating a process for determination of an identification means based on the information related to the abnormality candidate region illustrated in FIG. 2.

FIG. 5 is a flow chart illustrating a process, in which an identification means is determined based on the information related to the abnormality candidate region. At Step S131, the identifier selector 131 acquires the information related to the abnormality candidate region, that is, the type of abnormality, from the abnormality candidate information acquiring unit 120.

At subsequent Steps S132 to S136, the identifier selector 131 selects an identifier, based on the information related to the abnormality candidate region.

In detail, firstly, at Step S132, the identifier selector 131 determines whether or not the type of abnormality estimated for the abnormality candidate region is vascular abnormality. If the type is vascular abnormality (Step S132: Yes), the identifier selector 131 selects a color feature data identifier (Step S133). This is because: since a vascular abnormality region, such as bleeding, has a large difference particularly in color from a surface of a normal mucosal region; by use of color feature data, accurate identification is enabled. Specifically, a color feature data identifier, which executes identification based on color feature data, such as intensity of color ratios, hue, and chroma, in the abnormality candidate region, is selected. Thereafter, the process is returned to the main routine.

On the contrary, if the type of abnormality is not vascular abnormality (Step S132: No), the identifier selector 131 determines whether or not the type of abnormality is neoplastic abnormality (Step S134). If the type is neoplastic abnormality (Step S134: Yes), the identifier selector 131 selects a shape feature data identifier (Step S135). This is because: since a neoplastic abnormality region, such as a polyp, has a large difference particularly in shape from a surface structure of a normal mucosal region; by use of shape feature data, accurate identification is enabled. Specifically, a shape feature data identifier, which executes identification based on shape feature data, such as a circularity, an area, and a Feret's diameter, of the abnormality candidate region, is selected. Thereafter, the process is returned to the main routine.

On the contrary, if the type of abnormality is not neoplastic abnormality (Step S134: No), the identifier selector 131 determines that the type of abnormality is mucosal abnormality, and selects a color feature data identifier and a texture feature data identifier (Step S136). This is because: since a mucosal abnormality region, such as erosion or an ulcer, has a change in surface structure, with a change in color, such as redness or whiteness, based on inflammation, from a surface of a normal mucosal region; by use of, together with color feature data, texture feature data, more accurate identification is enabled. Specifically, the above described color feature data identifier is selected, and a texture feature data identifier, which executes identification based on texture feature data, such as high frequency component intensity, which have been calculated by LBP or DoG, is selected. Thereafter, the process is returned to the main routine.

At Step S14 subsequent to Step S13, the identification unit 140 executes identification of the abnormality candidate region by the identification means (identifier) determined in Step S13. An identification boundary used in each identifier is generated beforehand by a known means, such as a support vector machine (SVM). Thereby, whether or not the abnormality candidate region is an abnormal region is identified.

At subsequent Step S15, the arithmetic unit 100 outputs the identification result acquired in Step S14. Specifically, a flag indicating that an abnormal region has been detected is assigned to an intraluminal image with an abnormality candidate region identified as an abnormal region. In addition, a flag indicating the type of abnormality (vascular abnormality, neoplastic abnormality, or mucosal abnormality) may be assigned to the intraluminal image. Thereafter, the processing on the intraluminal image is ended.

As described above, in this first embodiment of the disclosure: an abnormality candidate region is detected from an intraluminal image; an estimated type of abnormality is acquired as information related to the abnormality candidate region; an identifier according to the type of abnormality is selected and used; and thereby, whether or not the abnormality candidate region is an abnormal region is identified. Thereby, influence of feature data not so related to the identification of whether or not the abnormality candidate region is abnormal is able to be eliminated, and accurate identification is enabled. Further, by selection of an appropriate identifier, the speed of the identification process is able to be increased.

Modified Example 1

Figure 6:
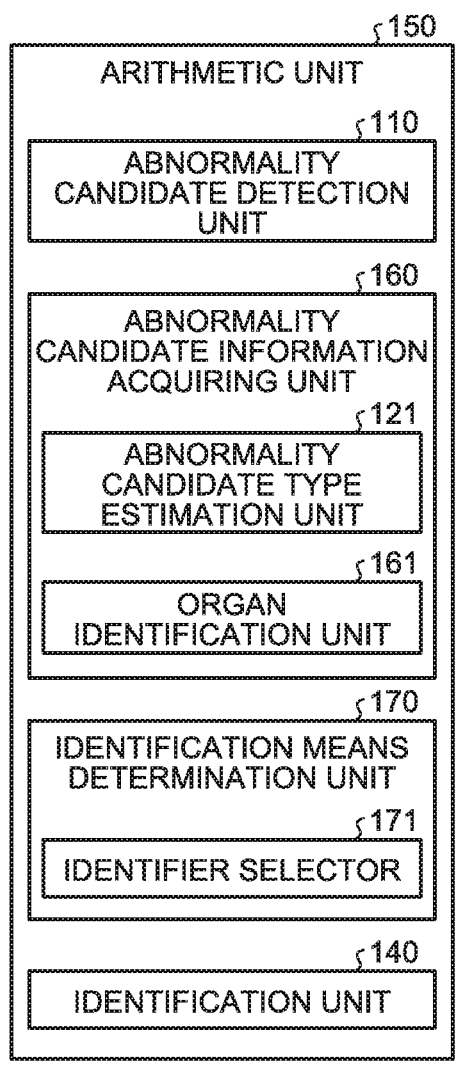
FIG. 6 is a block diagram illustrating a configuration of an arithmetic unit included in an image processing apparatus according to a modified example 1 of the first embodiment of the disclosure.

Next, a modified example 1 of the first embodiment of the disclosure will be described. FIG. 6 is a block diagram illustrating a configuration of an arithmetic unit included in an image processing apparatus according to this modified example 1. As illustrated in FIG. 6, the image processing apparatus according to this modified example 1 includes, instead of the arithmetic unit 100 illustrated in FIG. 1, an arithmetic unit 150. This arithmetic unit 150 includes, instead of the abnormality candidate information acquiring unit 120 and the identification means determination unit 130 that are illustrated in FIG. 1, an abnormality candidate information acquiring unit 160 and an identification means determination unit 170. A configuration and operation of each unit of this image processing apparatus other than the arithmetic unit 150, and a configuration and operation of the arithmetic unit 150 other than the abnormality candidate information acquiring unit 160 and the identification means determination unit 170 are the same as those of the first embodiment.

The abnormality candidate information acquiring unit 160 includes: an abnormality candidate type estimation unit 121 that determines a type of abnormality that an abnormality candidate region is estimated to belong to; and an organ identification unit 161 that identifies a type of organ, for which an intraluminal image to be processed has been captured; and the abnormality candidate information acquiring unit 160 acquires, as information related to the abnormality candidate region, a result of the estimation of the type of abnormality by the abnormality candidate type estimation unit 121 and a result of the identification of the type of organ by the organ identification unit 161. Operation of the abnormality candidate type estimation unit 121 is the same as that of the first embodiment.

Various known techniques may be applied to a process for the identification of the type of organ by the organ identification unit 161. For example, since organs, such as stomachs, small intestines, and large intestines, respectively have distinctive colors and textures, these organs are able to be identified based on color feature data and texture feature data. Specifically, they have characteristics that: mucosa of stomachs is comparatively redder; mucosa of small intestines is comparatively yellower and patterns of folds of villi are observed therein; and mucosa of large intestines is comparatively whiter while residues are observed therein. Thus, color feature data and texture feature data of the entire intraluminal image or a region other than the abnormality candidate region of the intraluminal image are calculated, degrees of coincidence with organ models acquired by prior learning are found, and thereby the type of organ is able to be identified. Specifically, by application of a feature vector based on color feature data and texture feature data of each organ acquired beforehand, to the decision index $P(x)$ given by the above described Equation (1), decision indices of the respective organs, specifically, a decision index $P(x)_{stomach}$ for stomachs, a decision index $P(x)_{small\ intestine}$ for small intestines, and a decision index $P(x)_{large\ intestine}$ for large intestines, are calculated, and the organ with the largest value of these decision indices is identified as the organ where the intraluminal image has been captured.

The identification means determination unit 170 includes an identifier selector 171 that selects an identifier, based on the type of abnormality estimated for the abnormality candidate region, and the organ, for which the intraluminal image has been captured. Abnormalities that occur in gastrointestinal tracts include abnormalities that differ in possibility of their occurrence according to types of organs. For example, main abnormalities in stomachs are erosion and ulcers. In this case, identification accuracy for color feature data and texture feature data is preferably increased. Further, main abnormalities in small intestines are bleeding. In this case, identification accuracy for color feature data is preferably increased. Main abnormalities in large intestines are tumors, such as polyps. In this case, identification accuracy for shape feature data is preferably increased.

Thus, the identifier selector 171 selects an identifier based on the type of abnormality and the type of organ. A method, in which an identifier selected according to the type of abnormality, and an identifier selected according to the type of organ are simply combined together, is one example of a method for the selection. For example, when the decision index $P(x)_{blood\ vessel}$ is the highest among the decision indices $P(x)_{blood\ vessel}$, $P(x)_{tumor}$ and $P(x)_{mucosa}$, and the decision index $P(x)_{stomach}$ is the highest among the decision indices $P(x)_{stomach}$, $P(x)_{small\ intestine}$, and $P(x)_{large\ intestine}$ of organs, based on the type of abnormality, a color feature data identifier having high identification accuracy for vascular abnormality is selected, and based on the type of organ, a color feature data identifier and a texture feature data identifier having high identification accuracy for erosion and ulcers that mainly occur in stomachs are selected. Therefore, as a combination (logical sum) of these identifiers, the color feature data identifier and texture feature data identifier are selected.

Second Embodiment

Figure 7:
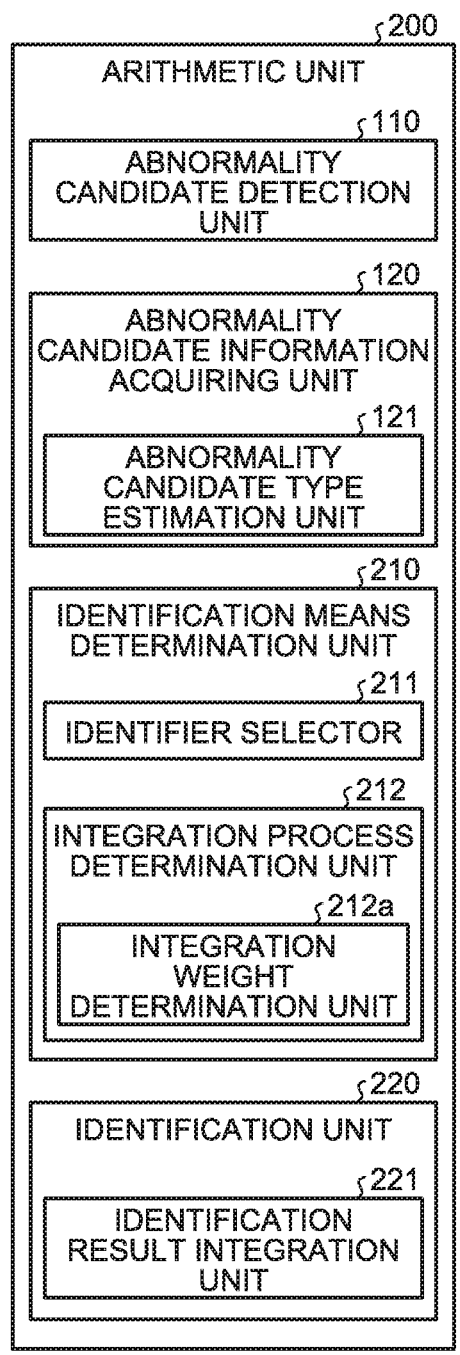
FIG. 7 is a block diagram illustrating a configuration of an arithmetic unit included in an image processing apparatus according to a second embodiment of the disclosure.

Next, a second embodiment of the disclosure will be described. FIG. 7 is a block diagram illustrating a configuration of an arithmetic unit included in an image processing apparatus according to a second embodiment of the disclosure. As illustrated in FIG. 7, the image processing apparatus according to this second embodiment includes, instead of the arithmetic unit 100 illustrated in FIG. 1, an arithmetic unit 200. This arithmetic unit 200 includes, instead of the identification means determination unit 130 and the identification unit 140 that are illustrated in FIG. 1, an identification means determination unit 210 and an identification unit 220. A configuration and operation of each unit of this image processing apparatus other than the arithmetic unit 200, and a configuration and operation of the arithmetic unit 200 other than the identification means determination unit 210 and the identification unit 220 are the same as those of the first embodiment.

The identification means determination unit 210 includes: an identifier selector 211 that selects more than one identifier for identification of one abnormality candidate region; and an integration process determination unit 212 that determines a process for integration of the more than one identifier selected by the identifier selector 211. The integration process determination unit 212 includes an integration weight determination unit 212a that determines weights used for integration of identification results by the selected more than one identifier.

The identification unit 220 includes an identification result integration unit 221 that integrates the more than one identification result by the more than one identifier selected by the identifier selector 211, and outputs, as a final identification result for the abnormality candidate region, the integrated identification results.

Figure 8:
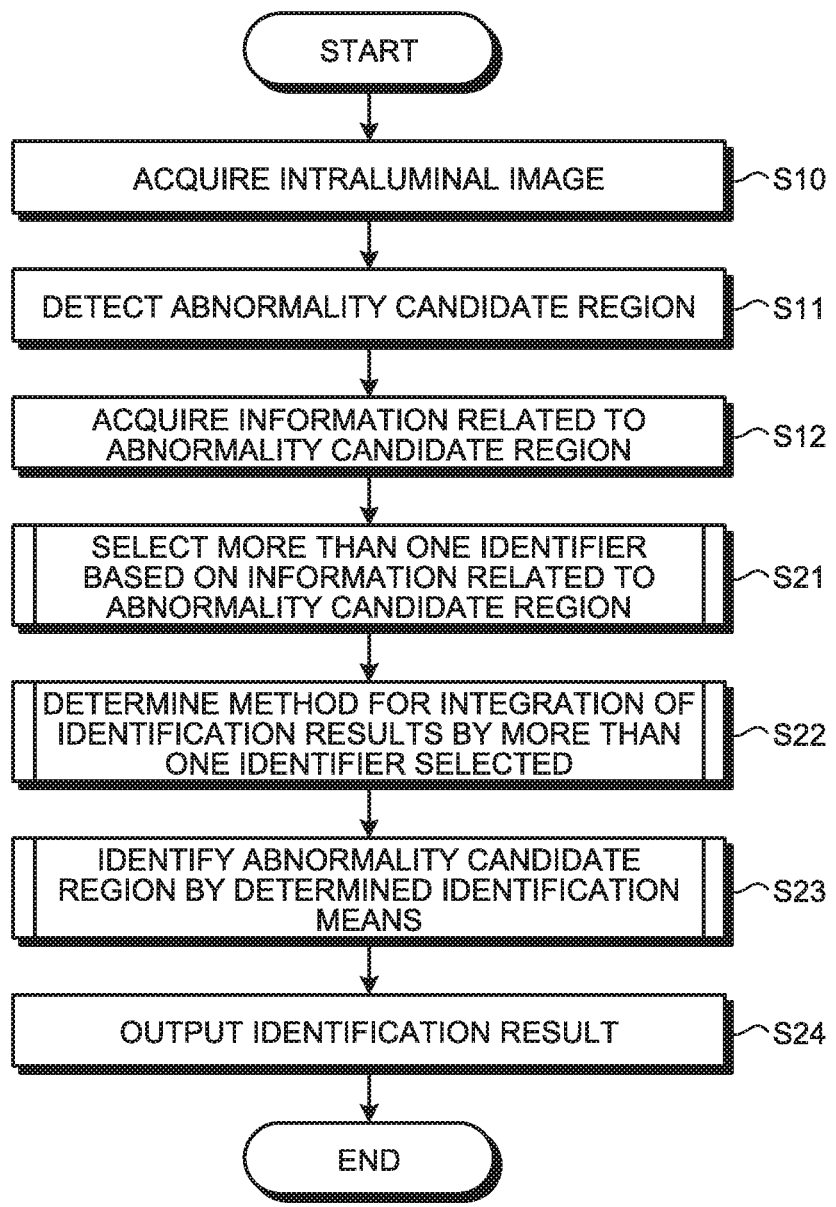
FIG. 8 is a flow chart illustrating operation of the image processing apparatus according to the second embodiment of the disclosure.

Next, operation of the image processing apparatus according to this second embodiment will be described. FIG. 8 is a flow chart illustrating the operation of the image processing apparatus according to the second embodiment. Steps S10 to S12 in FIG. 8 are the same as those of the first embodiment. Further, specific examples of color feature data, shape feature data, and texture feature data used in this second embodiment are the same as those described with respect to the first embodiment.

Figure 9:
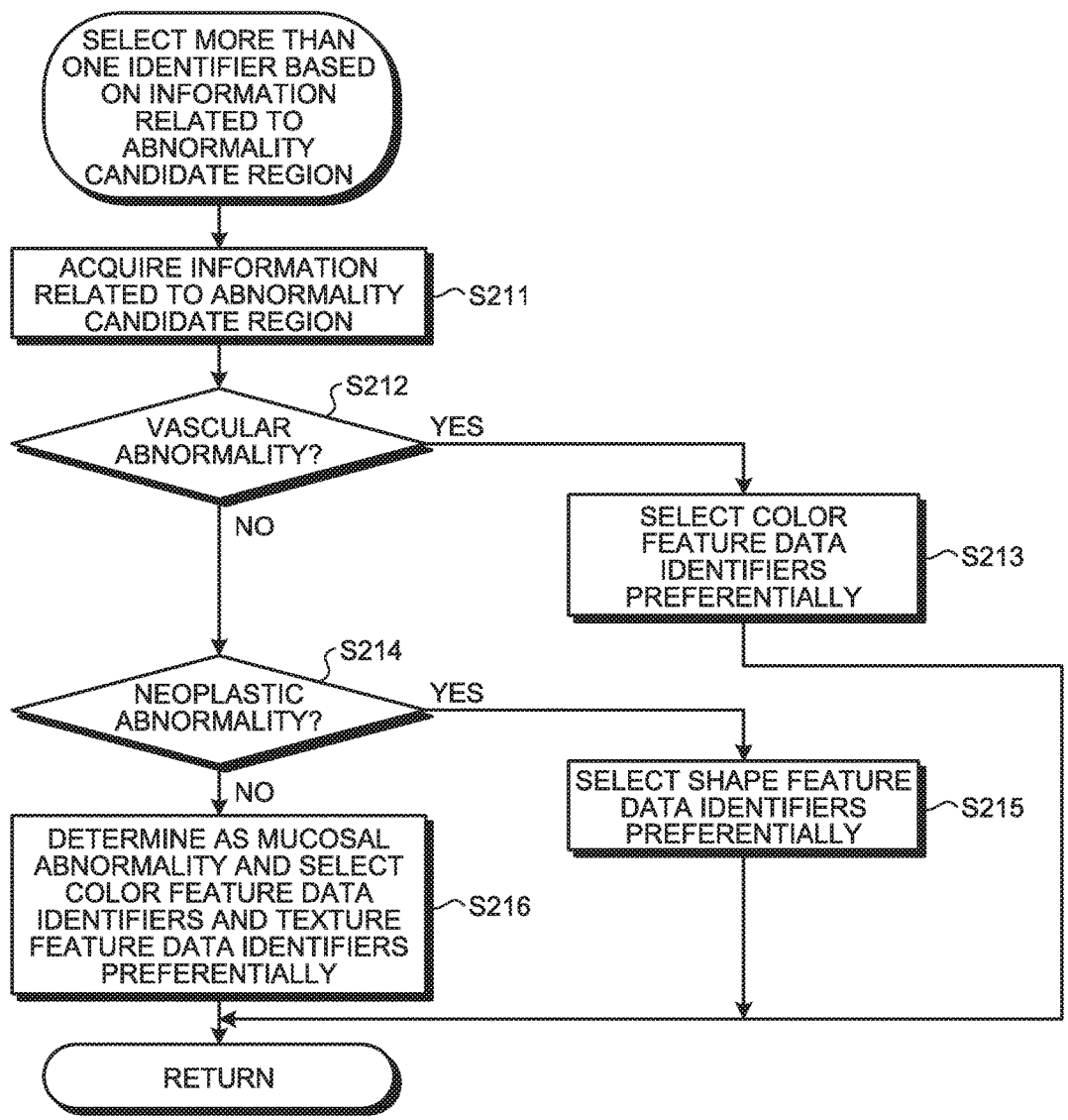
FIG. 9 is a flow chart illustrating a selection process for more than one identifier illustrated in FIG. 8.
Figure 10:
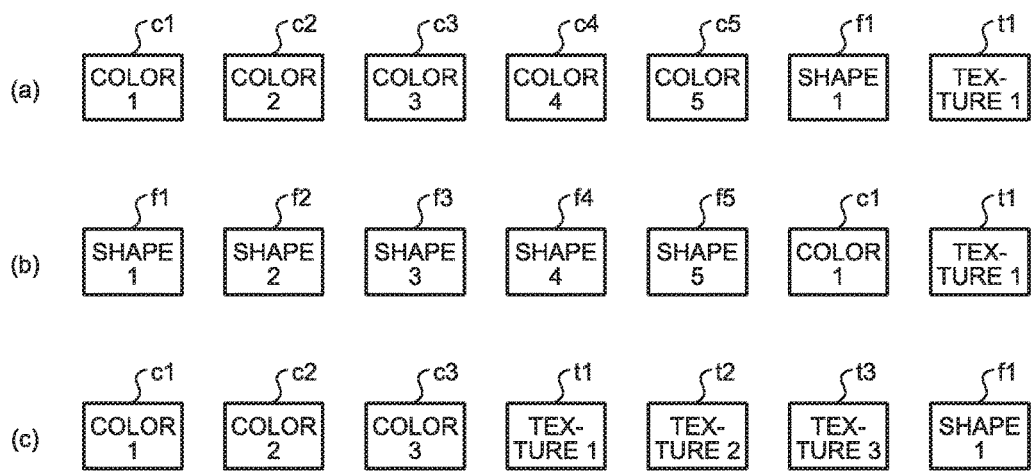
FIG. 10 is a schematic diagram for explanation of the selection process for more than one identifier illustrated in FIG. 9.

At Step S21 subsequent to Step S12, the identification means determination unit 210 selects more than one identifier, based on the information related to the abnormality candidate region acquired in Step S12. FIG. 9 is a flow chart illustrating a process for the selection of the more than one identifier. Further, FIG. 10 is a schematic diagram for explanation of the process for the selection of more than one identifier.

Firstly, at Step S211, the identifier selector 211 acquires the information related to the abnormality candidate region, from the abnormality candidate information acquiring unit 120. That is, the type of abnormality estimated for the abnormality candidate region is acquired.

At subsequent Steps S212 to S216, the identifier selector 211 selects more than one identifier, based on the information related to the abnormality candidate region.

A known learning method, such as bagging or boosting, in which the overall identifier is formed by combination of weak identifiers having simple identification abilities, for example, is used as a method of combining more than one identifier (reference: C. M. Bishop, "Pattern Recognition and Machine Learning, Last Volume", Springer Japan K.K., Pages 373 to 375). In FIG. 10, patterns, each of which has seven identifiers combined together, are illustrated, but the total number of identifiers to be included in one pattern is arbitrary, and not limited to seven. For example, by a user inputting the total number of identifiers via the input unit 30, the number of identifiers to be selected and combined may be set.

In detail, firstly, at Step S212, the identifier selector 211 determines whether or not the type of abnormality estimated for the abnormality candidate region is vascular abnormality. If the type is vascular abnormality (Step S212: Yes), the identifier selector 211 preferentially selects color feature data identifiers (Step S213).

Specifically, more color feature data identifiers are selected than shape feature data identifiers and texture feature data identifiers, the color feature data identifiers being for different types of color feature data. (a) of FIG. 10 is a schematic diagram illustrating a combination pattern of more than one identifier when color feature data identifiers are preferentially selected. In (a) of FIG. 10, an example, in which five types of color feature data identifiers c1 to c5, one type of shape feature data identifier f1, and one type of texture feature data identifier t1 are combined together, is illustrated.

Proportions of the selected numbers of color feature data identifiers, shape feature data identifiers, and texture feature data identifiers are not particularly limited, as long as the number of color feature data identifiers is large. These proportions may be of fixed values or variables. For example, according to proportions of the degrees of coincidence (decision indices $P(x)_{blood\ vessel}$, $P(x)_{tumor}$, and $P(x)_{mucosa}$) calculated in the estimation of the type of abnormality of the abnormality candidate region, the proportions of the selected numbers of the various identifiers may be determined. Thereafter, the process is returned to the main routine.

On the contrary, if the type of abnormality is not vascular abnormality (Step S212: No), the identifier selector 211 determines whether or not the type of abnormality is neoplastic abnormality (Step S214). If the type is neoplastic abnormality (Step S214: Yes), the identifier selector 211 preferentially selects shape feature data identifiers (Step S215). Proportions of the selected numbers of the various identifiers are not particularly limited, as long as the number of shape feature data identifiers is large. A method for the determination of the proportions is similar to that for vascular abnormality. (b) of FIG. 10 is a schematic diagram illustrating a combination pattern of more than one identifier when shape feature data identifiers are preferentially selected. In (b) of FIG. 10, an example, in which five types of shape feature data identifiers f1 to f5, one type of color feature data identifier c1, and one type of texture feature data identifier t1 are combined together, is illustrated. Thereafter, the process is returned to the main routine.

On the contrary, if the type of abnormality is not neoplastic abnormality (Step S214: No), the identifier selector 211 determines that the type of abnormality is mucosal abnormality, and preferentially selects color feature data identifiers and texture feature data identifiers (Step S216). Proportions of the selected numbers of various identifiers are not particularly limited, as long as the numbers of color feature data identifiers and texture feature data identifiers are large. A method for the determination of the proportions is similar to that for vascular abnormality. (c) of FIG. 10 is a schematic diagram illustrating a combination pattern of more than one identifier when color feature data identifiers and texture feature data identifiers are preferentially selected. In (c) of FIG. 10, an example, in which three types of color feature data identifiers c1 to c3, three types of texture feature data identifier t1 to t3, and one type of shape feature data identifier f1 are combined together, is illustrated. Thereafter, the process is returned to the main routine.

Figure 11:
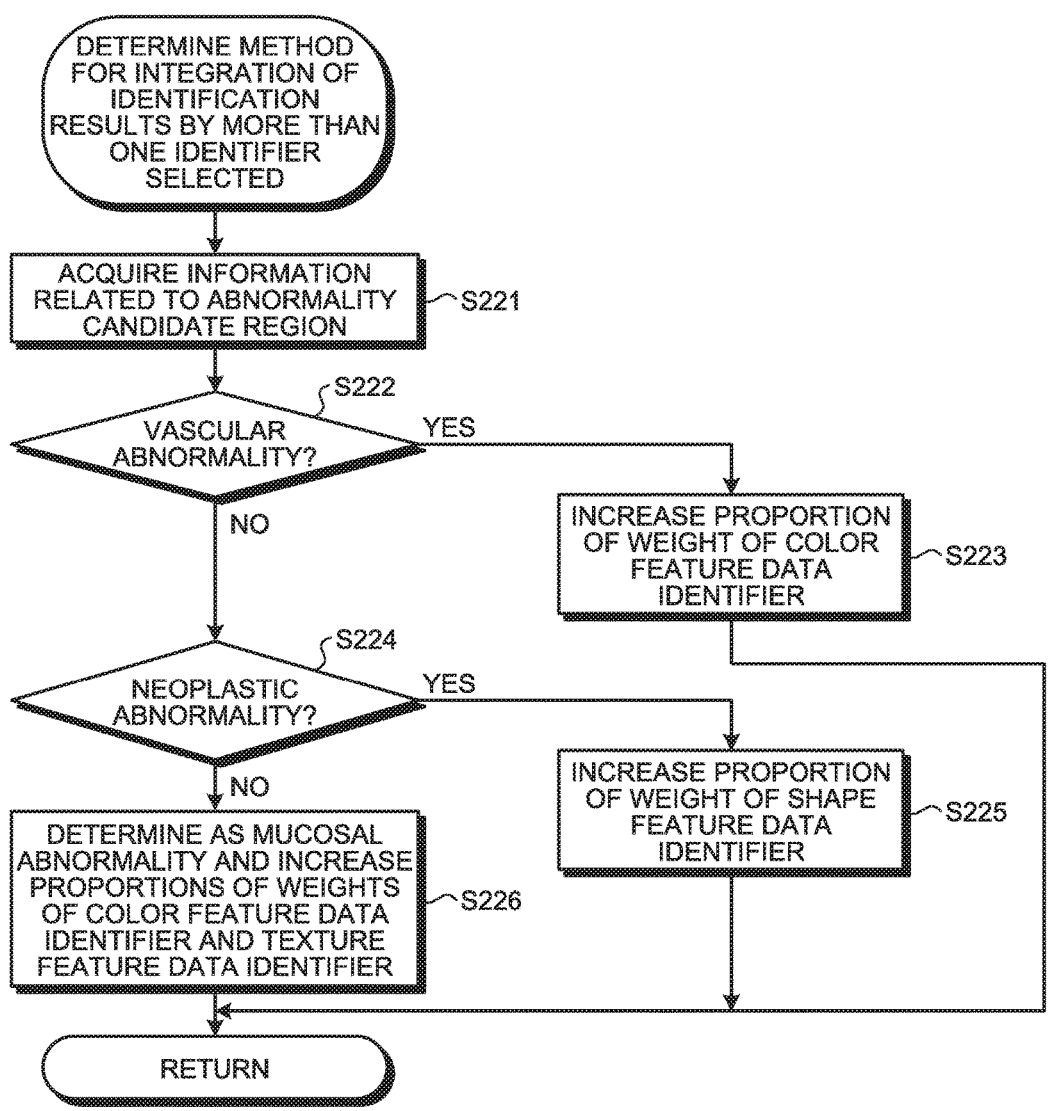
FIG. 11 is a flow chart illustrating a determination process for an integration method for the selected more than one identifier illustrated in FIG. 8.

At Step S22 subsequent to Step S21, the integration process determination unit 212 determines an integration method for the more than one identifier selected. FIG. 11 is a flow chart illustrating a process for the determination of the integration method for the more than one identifier selected.

Firstly, at Step S221, the integration process determination unit 212 acquires the information related to the abnormality candidate region.

At subsequent Steps S222 to S226, the integration weight determination unit 212a determines, based on the information related to the abnormality candidate region, proportions of weights given to identification results by the more than one identifier selected in Step S21.

If, at Step S21, plural identifiers $y_1$ to $y_m$ (where m is the total number of identifiers selected) are selected, the integration weight determination unit 212a determines weights $w_1$ to $w_m$ given to probabilities $P_1$ to $P_m$ that are respective identification results of these identifiers $y_1$ to $y_m$, such that the weights $w_1$ to $w_m$ change according to the type of abnormality estimated for the abnormality candidate region. The weights $w_1$ to $w_m$ are normalized such that the sum total becomes "1".

In detail, firstly, at Step S222, the integration weight determination unit 212a determines whether or not the type of abnormality estimated for the abnormality candidate region is vascular abnormality. If the type is vascular abnormality (Step S222: Yes), the integration weight determination unit 212a increases the proportion of the weight given to a color feature data identifier (Step S223) The proportion of the weight is not particularly limited as long as the weight given to the color feature data identifier is high, and may be of an arbitrary value. Or, a table indicating a relation between the information related to the abnormality candidate region (type of abnormality) and proportions of the weights may be generated beforehand, and by reference to this table, the proportions of the weights may be determined. Thereafter, the process is returned to the main routine.

On the contrary, if the type of abnormality is not vascular abnormality (Step S222: No), the integration weight determination unit 212a determines whether or not the type of abnormality is neoplastic abnormality (Step S224). If the type is neoplastic abnormality (Step S224: Yes), the integration weight determination unit 212a increases the proportion of the weight given to a shape feature data identifier (Step S225) A method of increasing the proportion of the weight is similar to that for vascular abnormality. Thereafter, the process is returned to the main routine.

On the contrary, if the type of abnormality is not neoplastic abnormality (Step S224: No), the integration weight determination unit 212a determines that the type of abnormality is mucosal abnormality, and increases the proportions of the weights given to a color feature data identifier and a texture feature data identifier (Step S226). A method of increasing the proportion of the weight is similar to that for vascular abnormality. Thereafter, the process is returned to the main routine.

Figure 12:
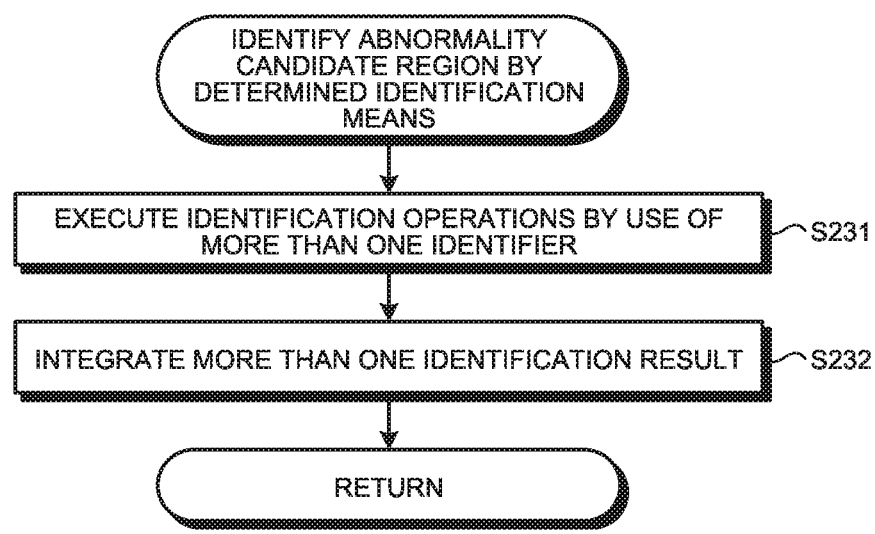
FIG. 12 is a flow chart illustrating an identification process for an abnormality candidate region by a determined identification means illustrated in FIG. 8.
Figure 13:
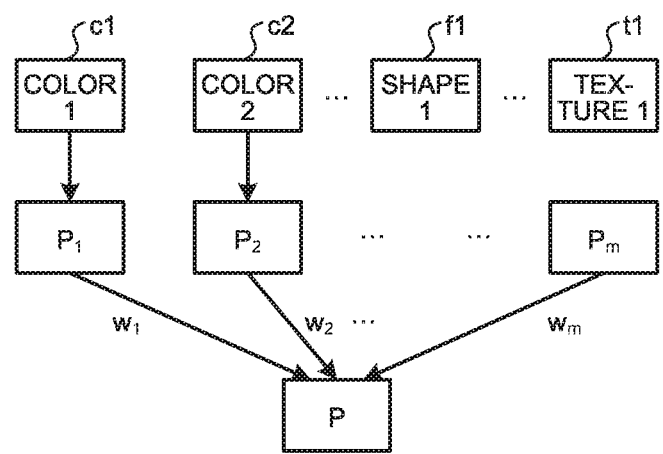
FIG. 13 is a schematic diagram for explanation of a process for integration of more than one identification result illustrated in FIG. 12.

At Step S23 subsequent to Step S22, the identification unit 220 identifies the abnormality candidate region by an identification means that has been determined. FIG. 12 is a flow chart illustrating a process for the identification of the abnormality candidate region by the determined identification means. Further, FIG. 13 is a schematic diagram for explanation of a process for integration of more than one identification result.

Firstly, at Step S231, the identification unit 220 executes identification operations by use of the more than one identifier selected through Step S21. Specifically, as illustrated in FIG. 13, identification operations by use of more than one identifier (for example, the color feature data identifiers c1, c2, . . . , the shape feature data identifier f1, the texture feature data identifier t1, and the like) are executed, and the probabilities $P_1$ to $P_m$ are acquired as identification results.

At subsequent Step S232, the identification result integration unit 221 integrates the more than one identification result output in Step S231, by the integration method determined in Step S22. That is, as expressed by Equation (2) below, by weighted summation being executed by use of the weights $w_1$ to $w_m$ given to the respective identifiers determined in Step S22, for the probabilities $P_1$ to $P_m$ acquired as the more than one identification result; an integrated identification result (probability P) is calculated.

$$P = P_1 \times w_1 + P_2 \times w_2 + \ldots + P_m \times w_m \quad (2)$$

Or, the identification result integration unit 221 may execute a more complicated weighted operation, instead of the weighted summation as expressed by Equation (2). For example, how the weights are given may be changed according to the value of the probability P, such that when the probability P is in a certain range, the probabilities $P_1$ to $P_m$ are simply multiplied by the weights $w_1$ to $w_m$, but when the probability P exceeds the certain range, the probabilities $P_1$ to $P_m$ are multiplied by values resulting from further multiplication of the weights $w_1$ to $w_m$ by a coefficient α. In this case, a calculation table for execution of the weighted operation may be generated beforehand, and by reference to this calculation table, the operation may be executed. Thereafter, the process is returned to the main routine.

At Step S24 subsequent to Step S23, the arithmetic unit 200 outputs the identification result acquired in Step S23. This output process is similar to that of the first embodiment. Thereafter, the processing on the intraluminal image is ended.

As described above, according to the second embodiment of the disclosure, more than one identifier is selected, with feature data identifiers suitable for identification of a type of abnormality being prioritized, according to the type of abnormality estimated for an abnormality candidate region, more than one identification result acquired by these identifiers is integrated after being weighted according to the type of abnormality, and thus an appropriate identification process is able to be executed according to the type of abnormality and an identification result that is more accurate is able to be acquired.

Modified Example 2-1

Next, a modified example 2-1 of the second embodiment of the disclosure will be described. In the above described second embodiment, weighted summation is executed according to a type of abnormality estimated for an abnormality candidate region, for identification results by more than one identifier that has been selected. However, without execution of this weighting, averaging may simply be executed. At Step S21, feature data identifiers of a specific type are preferentially selected according to the type of abnormality. For example, if a type of abnormality of an abnormality candidate region is vascular abnormality, more color feature data identifiers are selected than the other feature data identifiers. Therefore, even if identification results by these identifiers are averaged in equal proportion, contribution of identification results by the feature data identifiers of the specific type to the integrated identification result is able to be increased.

Modified Example 2-2

Next, a modified example 2-2 of the second embodiment of the disclosure will be described. In the above described second embodiment also, similarly to the modified example 1 of the first embodiment, the organ identification unit 161 may be provided (see FIG. 6), and selection of identifiers and determination of weights in consideration of a type of organ, for which an intraluminal image to be processed has been captured, may be executed.

Specifically, main abnormalities in stomachs are erosion and ulcers, and thus if the type of organ is stomach, the identifier selector 211 preferentially selects color feature data identifiers and texture feature data identifiers, such that identification accuracy for color and texture is increased. Further, the integration weight determination unit 212a increases proportions of weights given respectively to identification results by the color feature data identifiers and texture feature data identifiers.

Or, since main abnormalities in small intestines are bleeding, if the type of organ is small intestine, the identifier selector 211 preferentially selects color feature data identifiers. Further, the integration weight determination unit 212a increases proportions of weights given to identification results by the color feature data identifiers.

Further, since main abnormalities in large intestines are tumors, such as polyps, if the type of organ is large intestine, the identifier selector 211 preferentially selects shape feature data identifiers. Furthermore, the integration weight determination unit 212a increases proportions of weights given to identification results by the shape feature data identifiers.

When the weights are determined according to the type of organ, the probabilities $P_1$ to $P_m$, which are the identification results by the various identifiers, may be integrated together by Equation (3) below, for example, by use of the weights $w_1$ to $w_m$ determined according to the type of abnormality, and weights $w_1'$ to $w_m'$ determined according to the type of organ.

$$P = P_1 \times (w_1 + w_1') + P_2 \times (w_2 + w_2') + \ldots + P_m \times (w_m + w_m') \quad (3)$$

As another process in consideration of the type of organ, the identifier selector 211 may select more than one identifier based on the type of abnormality estimated for the abnormality candidate region, and the integration weight determination unit 212a may determine proportions of weights given to identification results by the respective identifiers according to the type of organ. Or, the identifier selector 211 may select more than one identifier by priority according to the type of organ, and the integration weight determination unit 212a may determine proportions of weights given to identification results by the respective identifiers according to the type of abnormality of the abnormality candidate region.

Third Embodiment

Figure 14:
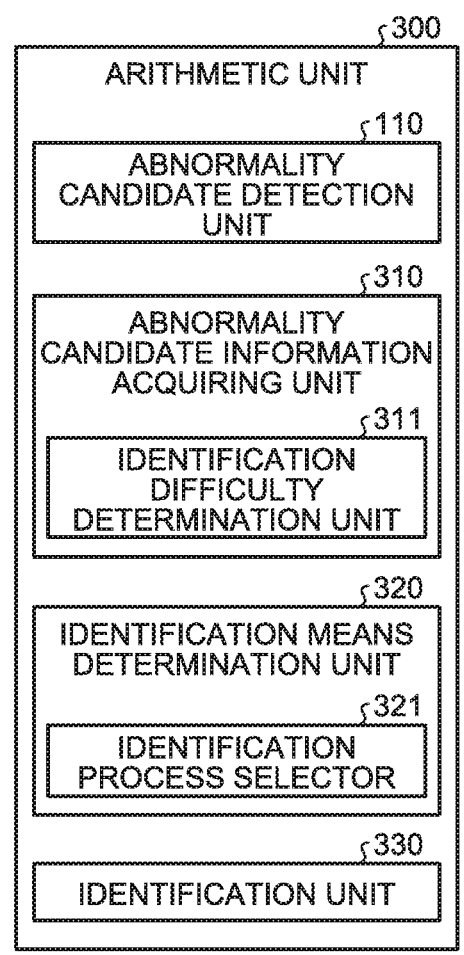
FIG. 14 is a block diagram illustrating a configuration of an arithmetic unit included in an image processing apparatus according to a third embodiment of the disclosure.

Next, a third embodiment of the disclosure will be described. FIG. 14 is a block diagram illustrating a configuration of an arithmetic unit included in an image processing apparatus according to the third embodiment. As illustrated in FIG. 14, the image processing apparatus according to this third embodiment includes, instead of the arithmetic unit 100 illustrated in FIG. 1, an arithmetic unit 300. This arithmetic unit 300 includes the abnormality candidate detection unit 110, an abnormality candidate information acquiring unit 310, an identification means determination unit 320, and an identification unit 330. Of these, operation of the abnormality candidate detection unit 110 is the same as that of the first embodiment.

The abnormality candidate information acquiring unit 310 includes an identification difficulty determination unit 311 that determines a difficulty of identification for the abnormality candidate region detected by the abnormality candidate detection unit 110, and outputs a result of the determination by the identification difficulty determination unit 311, as the information related to the abnormality candidate region. The difficulty of identification is determined based on the label assigned when the abnormality candidate region is detected (see Step S125 in FIG. 4). Specifically, the difficulty of identification is determined according to the type of abnormality (vascular abnormality, neoplastic abnormality, or mucosal abnormality) estimated for the abnormality candidate region.

The identification means determination unit 320 includes an identification process selector 321 that selects an identification means based on the difficulty of identification acquired as the information related to the abnormality candidate region. In detail, the identification process selector 321 selects a means for generating an identification boundary for when identification of whether or not the abnormality candidate region is an abnormal region is executed. Examples of the means for generating an identification boundary include the above mentioned bagging, a support vector machine, and classification by a linear discriminant function (reference: C. M. Bishop, "Pattern Recognition and Machine Learning, Last Volume", Springer Japan K.K., Pages 182 to 185). Classification by a linear discriminant function is a method, in which a linear discriminant function is found from data of two classes, a normal class and an abnormal class, as illustrated in (a) of FIG. 15, and classification is executed by application of this linear discriminant function to a new sample, as illustrated in (b) of FIG. 15.

The identification unit 330 identifies whether or not the abnormality candidate region is an abnormal region by using the identification means determined by the identification means determination unit 320.

Figure 16:
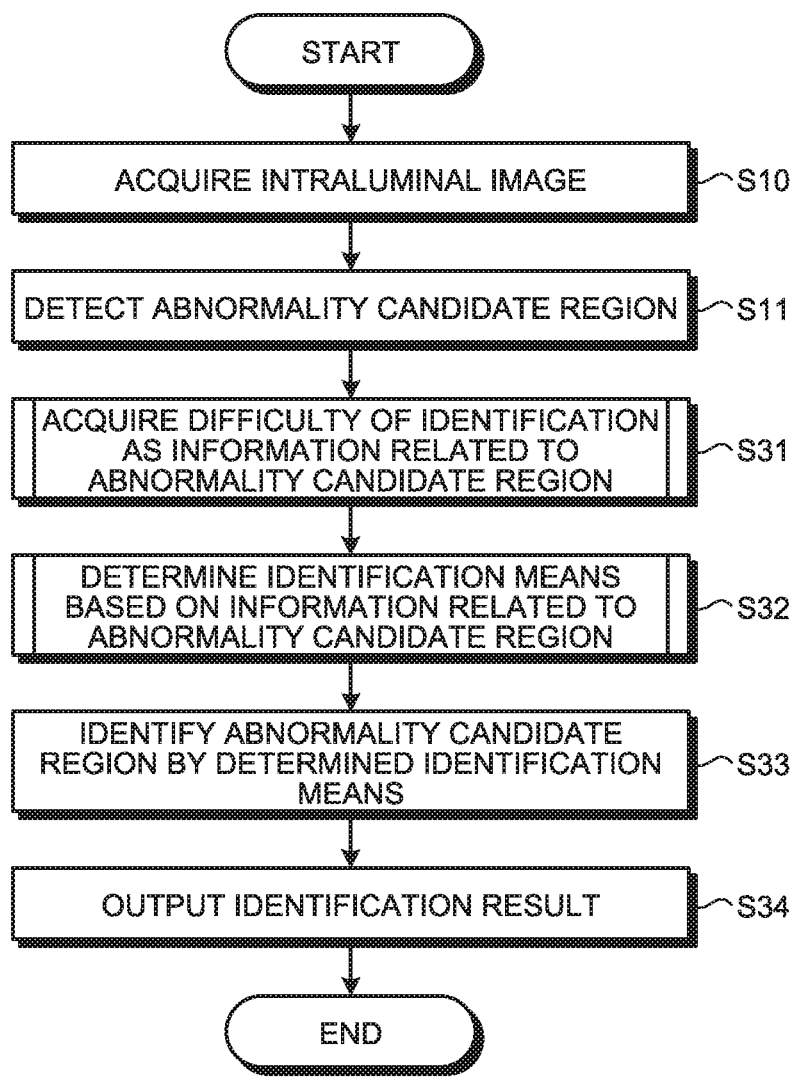
FIG. 16 is a flow chart illustrating operation of the image processing apparatus according to the third embodiment of the disclosure.

Next, operation of the image processing apparatus according to this third embodiment will be described. FIG. 16 is a flow chart illustrating the operation of the image processing apparatus according to this third embodiment. Steps S10 and S11 in FIG. 16 are the same as those of the first embodiment. Further, specific examples of color feature data, shape feature data, and texture feature data used in this third embodiment are the same as those described with respect to the first embodiment.

Figure 17:
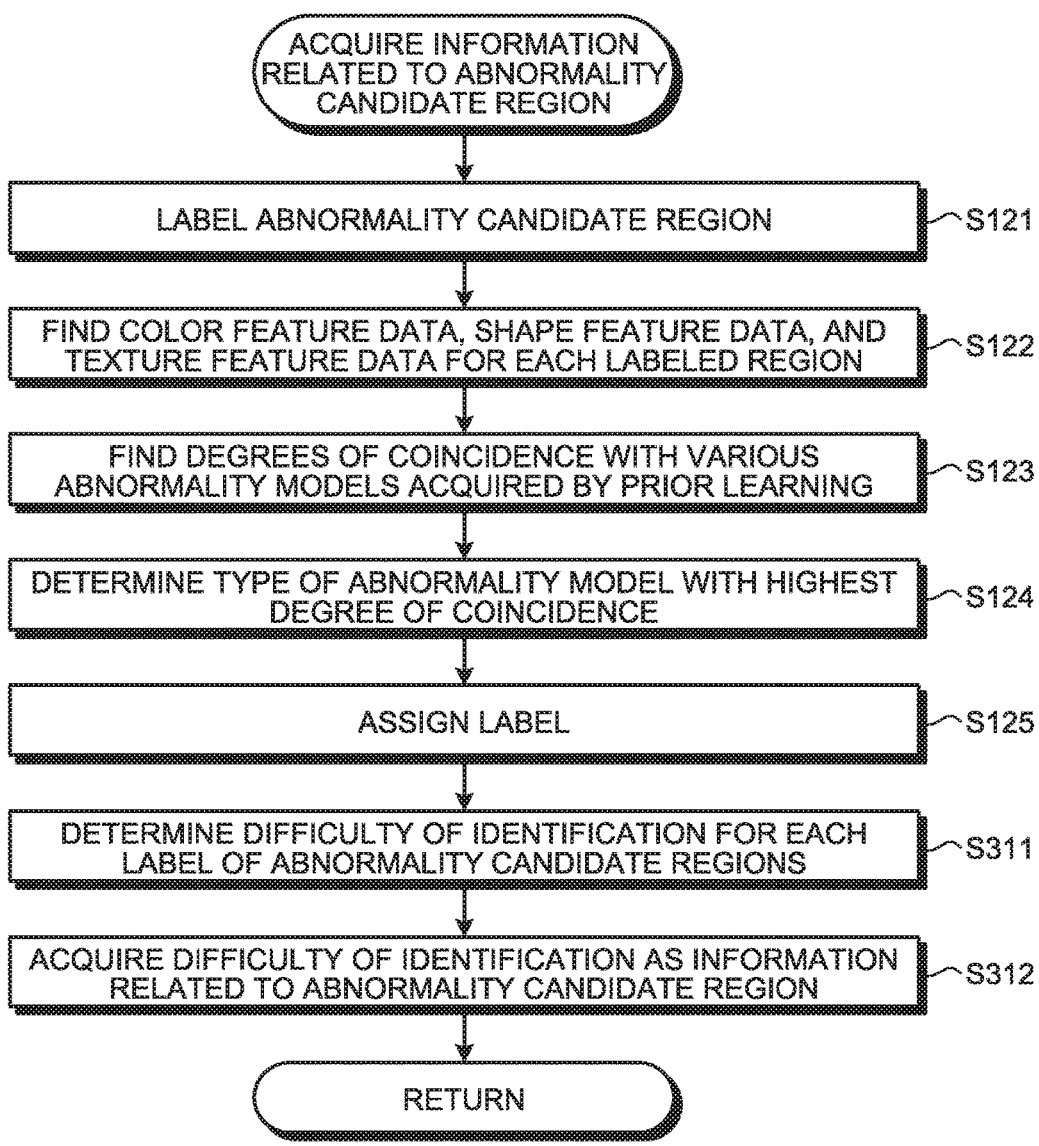
FIG. 17 is a flow chart illustrating an acquisition process for information related to an abnormality candidate region illustrated in FIG. 16.

At Step S31 subsequent to Step S11, the abnormality candidate information acquiring unit 310 acquires, as the information related to the abnormality candidate region, a difficulty of identification. FIG. 17 is a flow chart illustrating a process for the acquisition of the information related to the abnormality candidate region. Steps S121 to S125 in FIG. 17 are the same as those of the first embodiment (see FIG. 4).

At Step S311 subsequent to Step S125, the identification difficulty determination unit 311 determines a difficulty of identification for each label of abnormality candidate regions. Specifically, since vascular abnormality has a characteristic that color of bleeding is largely different from that of mucosa in gastrointestinal tracts, identification thereof is comparatively easy. Therefore, the identification difficulty determination unit 311 determines that a difficulty of identification of an abnormality candidate region assigned with a label of vascular abnormality is low. Further, although neoplastic abnormality has a characteristic shape, since a structure that may be misrecognized as a groove or the like may be present on a mucosal surface, and color thereof is similar to color of the mucosal surface, identification thereof is difficult. Therefore, the identification difficulty determination unit 311 determines that a difficulty of identification of an abnormality candidate region assigned with a label of neoplastic abnormality is high. Furthermore, since mucosal abnormality differs in how unevenness of a structure of a mucosal surface thereof looks, according to the image capturing environment, identification thereof is comparatively difficult. Therefore, the identification difficulty determination unit 311 determines that a difficulty of identification of an abnormality candidate region assigned with a label of mucosal abnormality is high.

As to levels of difficulty of identification: they may be binary with easy identification and difficult identification; more than one rank may be set from easy identification to difficult identification; or the difficulty of identification may be continuously set from easy identification to difficult identification. Further, these levels may be arbitrarily set by a user.

At subsequent Step S312, the abnormality candidate information acquiring unit 310 acquires the difficulty of identification determined by the identification difficulty determination unit 311, as the information related to the abnormality candidate region. Thereafter, the process is returned to the main routine.

At Step S32 subsequent to Step S31, the identification means determination unit 320 determines an identification means based on the information related to the abnormality candidate region acquired in Step S31, that is, the difficulty of identification. In detail, the identification process selector 321 generates an identification criterion for the abnormality candidate region, according to the difficulty of identification.

Figure 18:
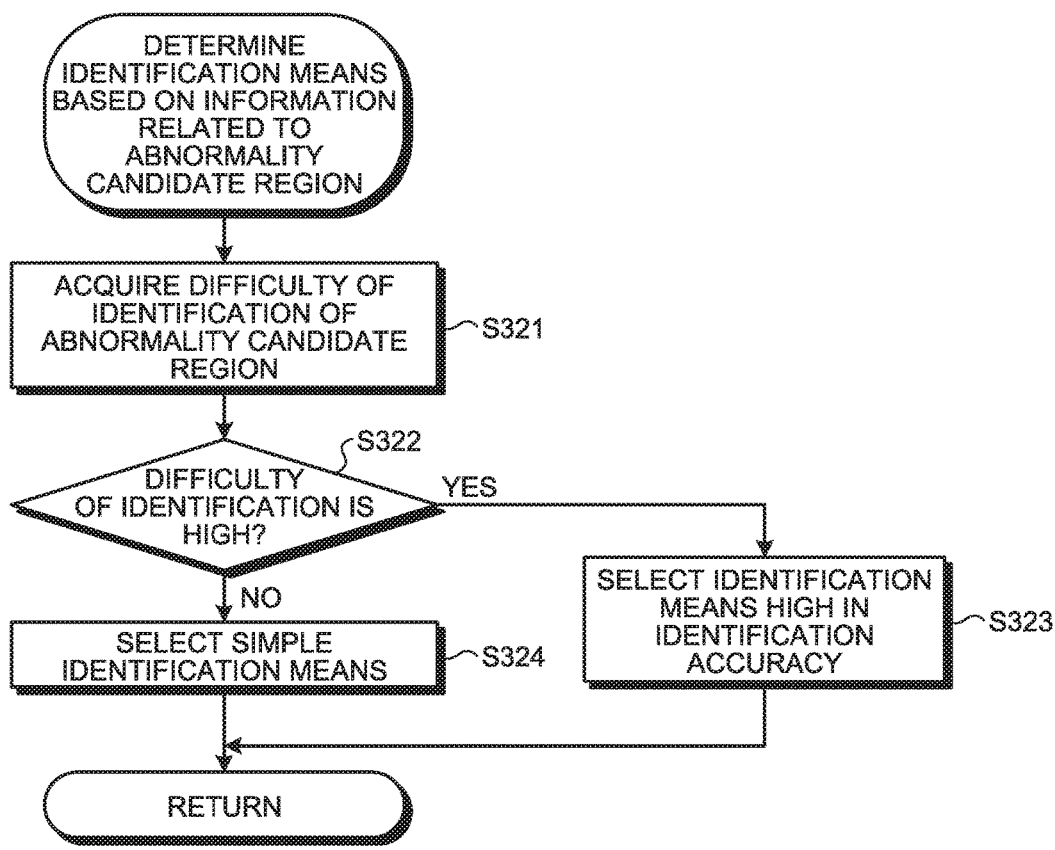
FIG. 18 is a flow chart illustrating a process for selection of an identification means illustrated in FIG. 16.

FIG. 18 is a flow chart illustrating a process for the selection of an identification means. Firstly, at Step S321, the identification process selector 321 acquires the difficulty of identification of the abnormality candidate region, from the abnormality candidate information acquiring unit 310.

At subsequent Step S322, the identification process selector 321 determines whether or not the acquired difficulty of identification is high.

At this step, if the difficulty of identification acquired from the abnormality candidate information acquiring unit 310 has been binarily set (between difficult identification and easy identification), the acquired difficulty of identification may be used as it is as the determination result. On the contrary, if the difficulty of identification acquired from the abnormality candidate information acquiring unit 310 has been set in more than one rank or continuously, the identification process selector 321 determines whether or not the difficulty of identification is high by executing threshold processing on the difficulty of identification. A threshold for that may be arbitrarily set by a user.

If the difficulty of identification is high (Step S322: Yes), the identification process selector 321 selects an identification means that is high in identification accuracy (Step S323). An identification means high in identification accuracy is generally a means that is complicated, and has a large number of dimensions of feature data and a large amount of calculation. Specifically, examples thereof include a nonlinear support vector machine, boosting, and the like.

On the contrary, if the difficulty of identification is not high (Step S322: No), that is, if the difficulty of identification is low, the identification process selector 321 selects a simple identification means (Step S324). A simple identification means is an identification means, which is not as high in identification accuracy as the means selected in Step S323, but is visually easy to be understood and is easy. Such an identification means is overwhelmingly low in scale of the number of dimensions of feature data and amount of calculation, as compared to the accurate identification means selected in Step S323. Specifically, examples thereof include a probability density function, classification by a linear discriminant function, a linear support vector machine, and the like. Thereafter, the process is returned to the main routine.

At Step S33 subsequent to Step S32, the identification unit 330 identifies the abnormality candidate region by the identification means determined in Step S32. In detail, the identification unit 330 generates an identification criterion by the means determined in Step S32, and by using this identification criterion, identifies whether or not the abnormality candidate region detected in Step S11 is an abnormal region.

At subsequent Step S34, the arithmetic unit 300 outputs the identification result acquired in Step S33. This output process is similar to that of the first embodiment. Thereafter, the processing on the intraluminal image is ended.

As described above, according to the third embodiment of the disclosure, an identification means is selected according to a difficulty of identification of an abnormality candidate region, and by use of the selected identification means, whether or not the abnormality candidate region is an abnormal region is identified. That is, for an abnormality candidate region high in difficulty of identification, an identification means that is large in amount of calculation, complicated, and high in identification accuracy is used, and for an abnormality candidate region low in difficulty of identification, an identification means that is not high in identification accuracy but is easy to be visually understood, simple, and small in amount of calculation is used. As described above, by use of an appropriate means according to a difficulty of identification of an abnormality candidate region, efficient identification is enabled with the necessary identification accuracy assured.

The above described first to third embodiments and modified examples thereof may be realized by an image processing program stored in a storage device being executed by a computer system, such as a personal computer or a work station. Further, such a computer system may be used by being connected to another computer system or a device, such as a server, via a local area network (LAN), a wide area network (WAN), or a public network, such as the Internet. In this case, the image processing apparatuses according to the first to third embodiments and modified examples thereof may acquire image data of intraluminal images via these networks, output image processing results to various output devices (viewers, printers, and the like) connected via these networks, and store the image processing results in storage devices (storage media and reading devices therefor, or the like) connected via these networks.

The disclosure is not limited to the first to third embodiments and the modified examples thereof, and various disclosures may be formed by combination, as appropriate, of more than one element disclosed in the respective embodiments and modified examples. For example, formation by exclusion of some elements from all of the elements illustrated in the respective embodiments and modified examples may be made, or formation by combination, as appropriate, of the elements illustrated in the different embodiments and modified examples may be made.

According to some embodiments, since a candidate region for a specific region is detected from an intraluminal image, and whether or not the candidate region is the specific region is identified based on an identification means determined based on information related to the candidate region; accurate identification is able to be executed by use of appropriate feature data and identifiers according to characteristics of the candidate region.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image processing apparatus, comprising:
    a hardware processor configured to:
        detect, from an image acquired by imaging inside a lumen of a living body, a candidate region for a specific region that is a region where a specific part in the lumen has been captured;
        acquire information related to the candidate region;
        determine a difficulty of identification of whether or not the candidate region is the specific region;
        select a type of identification for use in an identification of whether or not the candidate region is the specific region, wherein the selection is based on the information related to the candidate region and based on the difficulty of identification, and an identification accuracy of the selected type of identification is based on a type of the difficulty of identification; and
        identify whether or not the candidate region is the specific region by using the selected type of identification.

2. The image processing apparatus according to claim 1, wherein the hardware processor is configured to:
    in response to the identification difficulty being a binary high, select a type of identification of a first identification accuracy, wherein the first identification accuracy is associated with a first number of dimensions of feature data and a first amount of calculation; and
    in response to the identification difficulty being a binary low, select a type of identification of a second identification accuracy, wherein the second identification accuracy is associated with a second number of dimensions of feature data and a second amount of calculation, the second number of dimensions of feature data is less than the first number, and the second amount of calculation is less than the first amount.

3. The image processing apparatus according to claim 1, wherein the hardware processor includes an identifier selector configured to select, based on the information related to the candidate region, an identifier to be used in the identification of the candidate region, from one or more identifiers.

4. The image processing apparatus according to claim 3, wherein the hardware processor is configured to:
estimate a type of specific region that the candidate region belongs to, by using feature data of the image, and
select the identifier, based on the estimated type of specific region.

5. The image processing apparatus according to claim 3, wherein
the identifier selector is configured to select two or more identifiers from the one or more identifiers,
the hardware processor is configured to:
determine an integration process for integration of two or more identification results acquired respectively by the selected two or more identifiers, and
identify whether or not the candidate region is the specific region by integrating the two or more identification results together using the determined integration process.

6. The image processing apparatus according to claim 5, wherein the hardware processor is configured to:
estimate a type of specific region that the candidate region belongs to, by using feature data of the image, and
select the two or more identifiers by priority according to the estimated type of specific region.

7. The image processing apparatus according to claim 5, wherein the hardware processor is configured to determine two or more weights given respectively to the two or more identification results when the two or more identification results are integrated together.

8. The image processing apparatus according to claim 7, wherein the hardware processor is configured to:
estimate a type of specific region that the candidate region belongs to, by using feature data of the image, and
determine the two or more weights according to the estimated type of specific region.

9. An image processing method, comprising:
detecting, from an image acquired by imaging inside a lumen of a living body, a candidate region for a specific region that is a region where a specific part in the lumen has been captured;
acquiring information related to the detected candidate region;
determining a difficulty of identification of whether or not the candidate region is the specific region;
selecting a type of identification for use in an identification of whether or not the candidate region is the specific region, wherein the selection is based on the information related to the candidate region and based on the difficulty of identification, and the selected type of identification is high in identification accuracy when the difficulty of identification is high; and
identifying whether or not the candidate region is the specific region by using the selected type of identification.

10. A non-transitory computer-readable recording medium recording an image processing program that causes a computer to execute:
detecting, from an image acquired by imaging inside a lumen of a living body, a candidate region for a specific region that is a region where a specific part in the lumen has been captured;
acquiring information related to the detected candidate region;
determining a difficulty of identification of whether or not the candidate region is the specific region;
selecting a type of identification for use in an identification of whether or not the candidate region is the specific region, wherein the selection is based on the information related to the candidate region and based on the difficulty of identification, and the selected type of identification is high in identification accuracy when the difficulty of identification is high; and
identifying whether or not the candidate region is the specific region by using the selected type of identification.

11. An image processing apparatus, comprising:
a hardware processor configured to:
detect, from an image acquired by imaging inside a lumen of a living body, a candidate region for a specific region that is a region where a specific part in the lumen has been captured;
acquire information related to the candidate region;
select, based on the information related to the candidate region, two or more identifiers to be used in the identification of the candidate region, from a plurality identifiers;
determine an integration process for integration of two or more identification results acquired respectively by the selected two or more identifiers; and
identify whether or not the candidate region is the specific region by integrating the two or more identification results together using the determined integration process.

* * * * *